(12) United States Patent
Schewe et al.

(10) Patent No.: US 8,304,050 B2
(45) Date of Patent: Nov. 6, 2012

(54) MEDICAL DEVICE TUBING WITH DISCRETE ORIENTATION REGIONS

(75) Inventors: Scott Schewe, Eden Prairie, MN (US); Victor Schoenle, Greenfield, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 118 days.

(21) Appl. No.: 12/790,348

(22) Filed: May 28, 2010

(65) Prior Publication Data

US 2010/0233404 A1 Sep. 16, 2010

Related U.S. Application Data

(62) Division of application No. 10/617,428, filed on Jul. 10, 2003, now Pat. No. 7,727,442.

(51) Int. Cl.
*B29C 47/00* (2006.01)
*A61M 29/00* (2006.01)

(52) U.S. Cl. ... 428/36.9; 428/35.7; 604/915; 604/96.01; 604/103.06; 604/103.11; 604/103.13

(58) Field of Classification Search ............ 428/36.9, 428/35.7; 604/915, 96.01, 103.06, 103.11, 604/103.13
See application file for complete search history.

(56) References Cited

U.S. PATENT DOCUMENTS

| | | | |
|---|---|---|---|
| 2,940,126 A | 6/1960 | Sheridan | |
| 4,490,421 A | 12/1984 | Levy | |
| 4,720,384 A | 1/1988 | Di Luccio et al. | |
| 4,732,718 A | 3/1988 | Jentet | |
| 4,904,431 A | 2/1990 | O'Maleki | |
| 4,906,244 A | 3/1990 | Pinchuk et al. | |
| 4,935,190 A | 6/1990 | Tennerstedt | |
| 4,950,239 A | 8/1990 | Gahara et al. | |
| 4,963,313 A | 10/1990 | Noddin et al. | |
| 5,088,991 A | 2/1992 | Weldon | |
| 5,100,379 A * | 3/1992 | Wendell | 604/512 |
| 5,250,069 A | 10/1993 | Nobuyoshi et al. | |
| 5,264,260 A | 11/1993 | Saab | |
| 5,270,086 A | 12/1993 | Hamlin | |
| 5,304,340 A | 4/1994 | Downey | |
| 5,306,246 A | 4/1994 | Sahatjian et al. | |
| 5,316,706 A * | 5/1994 | Muni et al. | 264/472 |
| 5,328,468 A | 7/1994 | Kaneko et al. | |
| 5,342,386 A | 8/1994 | Trotta | |
| 5,344,400 A | 9/1994 | Kaneko et al. | |

(Continued)

FOREIGN PATENT DOCUMENTS

EP 0540858 5/1993

(Continued)

OTHER PUBLICATIONS

Introduction to Physical Polymer Science 3rd ed. Sperling, L.H., Wiley-Interscience, New York, 2001, p. 217-218.*

Primary Examiner — Michele L Jacobson
(74) Attorney, Agent, or Firm — Vidas, Arrett & Steinkraus, P.A.

(57) ABSTRACT

Medical device polymeric tubing segments suitable for forming catheter shafts or as balloon parisons are formed with discrete regions having different orientation relative to each other. Wall thickness may also be varied of the length of the segment.

5 Claims, 2 Drawing Sheets

U.S. PATENT DOCUMENTS

| | | | |
|---|---|---|---|
| 5,356,591 A | 10/1994 | Pinchuk et al. | |
| 5,403,340 A | 4/1995 | Wang et al. | |
| 5,500,180 A | 3/1996 | Anderson et al. | |
| 5,525,388 A | 6/1996 | Wand et al. | |
| 5,556,383 A | 9/1996 | Wang et al. | |
| 5,587,125 A | 12/1996 | Roychowdhury | |
| 5,605,543 A | 2/1997 | Swanson | |
| 5,614,136 A | 3/1997 | Pepin et al. | |
| 5,622,665 A | 4/1997 | Wang | |
| 5,643,279 A | 7/1997 | Trotta | |
| 5,714,110 A | 2/1998 | Wang et al. | |
| 5,725,814 A | 3/1998 | Harris | |
| 5,738,653 A | 4/1998 | Pinchuk et al. | |
| 5,741,452 A | 4/1998 | Ryan et al. | |
| 5,797,877 A | 8/1998 | Hamilton et al. | |
| 5,891,110 A * | 4/1999 | Larson et al. | 604/523 |
| 5,948,345 A | 9/1999 | Patel et al. | |
| 6,024,722 A * | 2/2000 | Rau et al. | 604/96.01 |
| 6,045,547 A | 4/2000 | Ren et al. | |
| 6,110,142 A | 8/2000 | Pinchuk et al. | |
| 6,136,056 A | 10/2000 | Krehan | |
| 6,146,356 A | 11/2000 | Wang et al. | |
| 6,156,254 A | 12/2000 | Andrews et al. | |
| 6,168,748 B1 | 1/2001 | Wang et al. | |
| 6,176,698 B1 | 1/2001 | Grantz et al. | |
| 6,270,522 B1 | 8/2001 | Simhambhatla et al. | |
| 6,325,780 B1 * | 12/2001 | Schaible et al. | 604/103.06 |
| 6,328,710 B1 | 12/2001 | Wang et al. | |
| 6,436,056 B1 | 8/2002 | Wang et al. | |
| 6,443,925 B1 * | 9/2002 | Schaible et al. | 604/96.01 |
| 6,458,313 B2 | 10/2002 | Hudgins et al. | |
| 6,465,067 B1 | 10/2002 | Wang et al. | |
| 6,500,146 B1 | 12/2002 | Pinchuk et al. | |
| 6,500,148 B1 | 12/2002 | Pinchuk et al. | |
| 6,562,021 B1 | 5/2003 | Derbin et al. | |
| 6,572,813 B1 | 6/2003 | Zhang et al. | |
| 6,579,484 B1 * | 6/2003 | Tiernan et al. | 264/173.16 |
| 6,663,614 B1 | 12/2003 | Carter | |
| 6,905,743 B1 | 6/2005 | Chen et al. | |
| 7,029,732 B2 | 4/2006 | Wang et al. | |
| 7,128,862 B2 * | 10/2006 | Wang | 264/171.29 |
| 7,128,956 B2 * | 10/2006 | Wang et al. | 428/36.9 |
| 7,387,826 B2 * | 6/2008 | Burgmeier et al. | 428/35.7 |
| 7,601,285 B2 * | 10/2009 | Burgmeier et al. | 264/211 |
| 7,727,442 B2 | 6/2010 | Schewe et al. | |
| 7,744,973 B2 * | 6/2010 | Schoenle et al. | 428/36.9 |
| 7,842,024 B2 * | 11/2010 | Burgmeier et al. | 604/525 |
| 2002/0081404 A1 * | 6/2002 | Schaible et al. | 428/35.2 |
| 2002/0150707 A1 * | 10/2002 | Wilkins | 428/35.2 |
| 2003/0009114 A1 * | 1/2003 | Chin et al. | 600/585 |
| 2003/0009151 A1 * | 1/2003 | Wang | 604/526 |
| 2003/0100869 A1 * | 5/2003 | Wang | 604/264 |
| 2005/0008806 A1 * | 1/2005 | Schewe et al. | 428/36.9 |
| 2005/0146085 A1 * | 7/2005 | Holman et al. | 264/535 |
| 2010/0010439 A1 * | 1/2010 | Burgmeier et al. | 604/96.01 |

FOREIGN PATENT DOCUMENTS

| | | |
|---|---|---|
| JP | 2002-331034 | 11/2002 |
| WO | 98/03218 | 1/1998 |
| WO | 00/01420 | 1/2000 |

\* cited by examiner

MEDICAL DEVICE TUBING WITH DISCRETE ORIENTATION REGIONS

CROSS-REFERENCE TO RELATED APPLICATIONS

This application is a Division of U.S. application Ser. No. 10/617,428, filed Jul. 10, 2003, the entire contents of which are hereby incorporated herein by reference.

BACKGROUND OF THE INVENTION

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices vary according to the specific application, but for many applications a high strength robust balloon is necessary and good softness and trackability properties are highly desirable.

Commercial high strength balloons having wall strengths in excess of 20,000 psi, have been formed of a wide variety of polymeric materials, including PET, nylons, polyurethanes and various block copolymer thermoplastic elastomers. U.S. Pat. No. 4,490,421, Levy and U.S. Pat. No. 5,264,260, Saab describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al and U.S. Pat. No. 6,146,356, Wang et al, describes balloons made from polyether-block-amide copolymers and polyester-block-ether copolymers. U.S. Pat. No. 6,270,522 Simhambhatla, et al, describes balloons made from polyester-block-ether copolymers of high flexural modulus. U.S. Pat. No. 5,344,400, Kaneko, describes balloons made from polyarylene sulfide. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons.

Different balloon materials provide different properties. In general, materials with high elongation and low flexural modulus give relatively greater resistance to pin hole formation and to winging upon deflation and also provide better trackability through body lumens, but such materials tend to give balloons with lower burst strengths and higher distensibility. Conversely, polymer materials with relatively high tensile strengths and hardness tend to give balloons with low distension and high burst strengths, but at a sacrifice of susceptibility to pin holing, winging and/or loss of trackability.

A variety of blow forming techniques have been utilized. The extruded parison may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents already mentioned or in U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al.

Following blow-forming the balloons may be simply cooled, heat set at a still higher pressure and/or temperature or heat shrunk at an intermediate pressure and/or temperature, relative to the blow forming temperature and pressure. See U.S. Pat. No. 5,403,340, Wang et al, EP 540858 Advanced Cardiovascular Systems, Inc., WO 98/03218, Scimed Life Systems.

It has been recognized that a single die can be used to produce different tubing diameters by varying the draw down ratio, but, at least since the advent of PET balloons, relatively low draw down ratios have been recommended to provide an amorphous state and thereby facilitate the subsequent blow-forming step. See S. Levy, "Improved Dilatation Catheter Balloons," *J. Clinical Engineering*, Vol. 11, No. 4, July-August 1986, 291-295, at p 293.

Thus a great deal of attention has been paid to blow forming processing conditions and to balloon materials. Until recently less attention has been paid to extrusion conditions for preparing the polymer tubing used as the parison.

In commonly owned copending U.S. application Ser. No. 10/087,653, filed Feb. 28, 2002, incorporated herein by reference, it is disclosed that improved balloon properties can be obtained by controlling the parison extrusion in a manner which restricts the elongation of the parison material in the longitudinal direction. The application discloses that decreasing the gap between the extrusion head and the cooling bath tank can lower parison elongation by shortening the quench time. Quench time can also be shortened by increasing the line speed.

For catheter shafts, it has long been recognized that the proximal shaft portion should have high torqueability and therefore should be relatively stiff, whereas the distal shaft portions desirably should have high flexibility. It is also desirable that the transition to high flexibility be gradual to minimize kinking and to more effectively transfer push and rotation forces to the end of the catheter. Typically this will be accomplished by a combination of structural features, including reinforcement in the proximal region, a more distal transition to unreinforced polymer, and/or a change of polymer material in a distal region. However, other techniques which allow smoother transitions, greater variation in shaft properties, cheaper or faster manufacture, or the like, remain desirable.

SUMMARY OF THE INVENTION

The present invention is directed to methods of forming extruded tubular polymeric segments with a varied orientation or elongation along the length thereof. That is, there are at least two portions of the tubular segments which have different orientation or elongation properties, relative to each other. The extruded tubular polymeric segments may be, for instance, catheter shafts or shaft portions or parisons for forming balloons.

Another aspect of the invention is an extrusion method for forming a tubular segment in a manner that produces a varying orientation or elongation along its length. In the case of balloons the segment will typically be provided with higher orientation and lower elongation, in the region used to form the balloon body portions than is obtained in regions used to form the balloon cones and waists. In the case of catheter shaft portions the region of the tube forming the most proximal portion will typically be formed with the higher orientation and lower elongation, relative to the more distal region(s).

Further aspects of the invention are described in the following detailed description of the invention or in the claims.

DETAILED DESCRIPTION OF THE INVENTION

Figure 1:
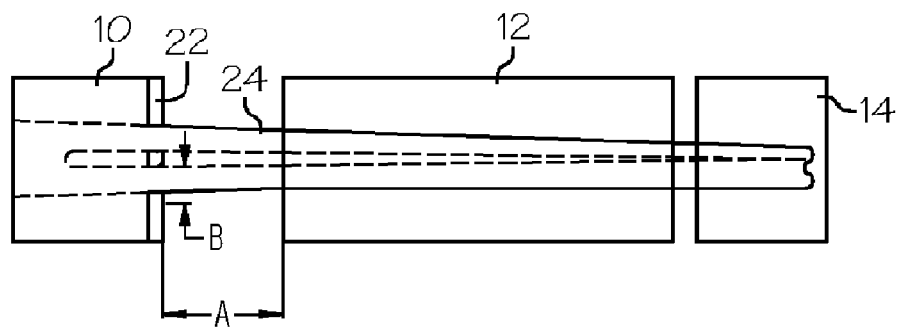
FIG. 1 is a schematic depiction of an extrusion system useable in the invention.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

A variety of processes are used to blow balloons from tubular parisons and the processes used may be adapted to use the parisons produced in accordance with the present invention. For any given balloon blowing process, portions of balloon parisons will be slated to become the waist, cone or body. This is usually done inherently, simply by mounting the parison in a prescribed manner and following a prescribed blowing program.

As described in copending U.S. application Ser. No. 10/087,653, it has been found that the distention and the burst pressure of a balloon are affected by the elongation properties of the extruded parison, as well as by the hoop ratio and the tube wall thickness. The elongation properties of the tubular parison can be increased or decreased by changing various extrusion conditions, particularly the quench time. Quench time can be changed by changing the gap between the extrusion die and the cooling tank, or by changing the line speed of the extrusion. Without being bound thereto, the elongation property changes are understood to be an inverse function of the degree of orientation, that is, as orientation is increased, elongation is decreased.

The present invention utilizes novel manufacturing techniques to discreetly alter extruded tubing orientation properties and/or wall thickness along the length of a single tubing segment. In accordance with one aspect of the invention if the tank gap is changed in the course of extrusion of a tube segment, the orientation properties of the segment will vary correspondingly.

At the same time, or alternatively, the die opening or the line speed of the tube may be changed to vary wall thickness along the length of the tubing segment. Accordingly much more complex tubing properties and/or configurations may be obtained.

The invention has application to the preparation of pre-formed balloon parisons, and also to the preparation of catheter shafts that will make it possible to selectively reduce the cross section wall area and polymer orientation properties of the extrusion.

In a balloon application, the selective orientation and tube wall reduction allows the balloon parison and resulting molded balloon to have new properties that are not currently possible. Especially with larger balloons the limiting factor in producing a balloon with small waist diameters generally has been that the balloon parison waist diameters are larger than the desired final molded balloon waist diameters if sufficient material is to be provided to the balloon body portion.

Typically, most balloons larger than 6 mm in diameter are fixtured on 0.035" (0.889 mm) wire size compatible catheter systems. Balloons smaller than 6 mm in diameter are typically fixtured on 0.014" (0.356 mm) or 0.018" (0.457 mm) wire compatible catheter systems. The main reason for this is the challenge of maintaining the properties of the balloon body while simultaneously reducing the material thickness of the balloon cones and waist area. It would be advantageous in some cases to provide balloons larger than 6 mm on a smaller wire diameter.

In some embodiments of the invention, waist sections of the molded balloon can be produced with higher material strength (tensile & hoop strength will be increased) beyond that available with current balloon manufacturing processes. Further, in some embodiments of the invention the initial balloon parison waist dimensions can now be reduced further relative to parison body dimension, thereby enabling larger balloons to be made and employed on smaller guide wire systems.

In a catheter shaft application, selective orientation and tube wall reduction enables a continuous tapered shaft from one material without the need for distal shaft bonds.

It is known that the gap between the extrusion head die and the cooling medium can be adjusted to alter molecular orientation of the extruded polymer tubing. In general, increasing the gap between the extrusion die and the cooling medium will yield lower levels of polymer orientation due to fact that the polymer is allowed to 'relax' and recoil from it's highly orientated state when exiting the extrusion head die. Conversely, when the gap is minimized, the polymer does not have as much time to 'relax' and the polymer is solidified in a more highly orientated state.

In the practice of developing balloon parison 'pre-forms', it is desirable to combine the above polymer orientation with specific areas of reduced tubing cross-sectional area. The areas of low polymer orientation and reduced cross-section area would make up the cone and waist area of the balloon Referring to FIG. 1, there is shown a schematic of an extrusion system comprising an extrusion head 10, coolant tank 12 and take up unit 14. In the extrusion head 10, liquefied polymer is pumped through a die head 22, emerging as a tube 24 which is quenched as it passes through the coolant tank 12. The coolant tank 12 is spaced by a tank gap A. In accordance with one aspect of the invention, the tank gap A is varied during the extrusion, so that it changes over the length of a discrete segment of the tubing. In this way a varied elongation or orientation characteristic is obtained. Alternatively, a similar effect may be obtained by varying the line speed of the extruded tube over the segment length so that residence time passing through a fixed tank gap A is varied.

Preferably the tube 24 is extruded continuously, with the tank gap cycling back to the initial position after each segment run in a periodic manner which repeats the desired segment at regularly spaced intervals. The tube 24 may be cut into the desired segment as part of the take-up processing, preferably using a cutter delay synchronized with the tank gap controller so that the orientation reproducibly occurs at the desired positions along the tubing segment. Alternatively the tube 24 may be cut into segments at a later time after identifying a suitable starting position, for instance by observing birefringence changes observable using polarized light filters, or with reference to a marker placed on the tube at a predetermined location according to an established relationship to the orientation cycle.

Figure 2:
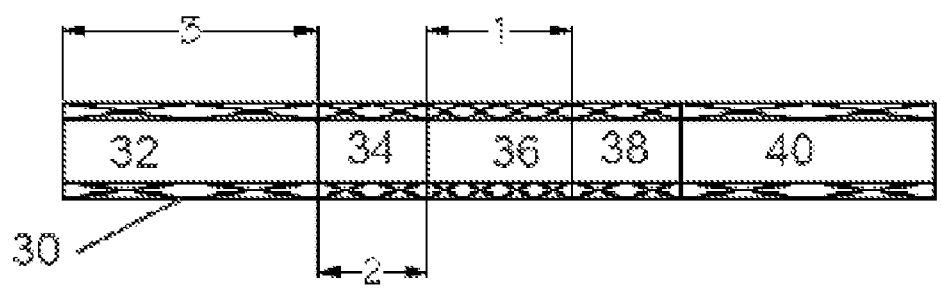
FIGS. 2 and 3 are representations of two different extruded balloon parisons of the invention, depicting variations in orientation along the length thereof.

FIG. 2 shows an extruded parison 30 prepared in accordance with this aspect of the invention, with crosshatching indicating the variation in orientation obtained. The segment has five distinct regions 32, 34, 36, 38, 40, each with different levels of orientation. Regions 32 and 40 have a low level of orientation created by the tank gap at the max gap setting. Region 36 has a high level of orientation, created with the tank gap at the minimum gap setting. Regions 34 and 38 are transition regions in which orientation changes, corresponding to the movement of the tank gap from one setting to the other. At constant line speed, the length of regions 34 and 38 are governed by the speed of the transition between the minimum and maximum gap lengths, whereas the lengths of regions 32, 36 and 40 are governed by relative times held at the minimum and maximum positions. In subsequent processing operations region 36 will form the balloon body, regions 34, 38 will form the cones and regions 32, 40, the waists of a medical device balloon.

More complex patterns are also available. Stepped transitions may be produced, the length of transition region 34 may be different from that of region 38, and/or the gap settings for the regions 32 and 40 may be different.

For catheter shaft tubing, the gap may be gradually changed from a minimum to a maximum value (or vice versa) over the entire length of the shaft segment. This may be optionally done with a concurrent alteration of the tubing wall thickness so that the wall thickness decreases as the gap lengthens. In this way an entire catheter shaft can be prepared having a continuous tapering wall thickness, high torqueability at the proximal end and high flexibility at the distal end from a single length of tubing. The same principles can be applied to the formation of either proximal or distal catheter shaft portions in a conventional shaft construction joined portions.

Using elongation at yield to measure orientation, differences in orientation of as much as 30% can be obtained over the length of a balloon parison or catheter shaft or shaft portion. In a preferred embodiment the orientation difference provides at least a 20% reduction in elongation in the body slated portion of a balloon parison relative to a waist slated portion.

Figure 3:
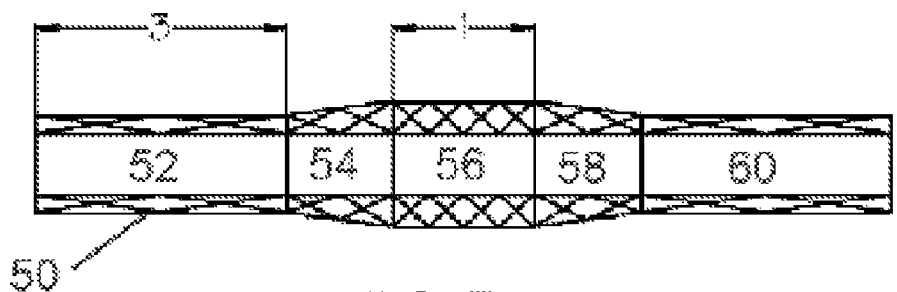

FIG. 3 shows a tubing segment 50 for a balloon parison having a variation of orientation over the length, varying in transition region 54 from the minimum of region 52 to the maximum at central region 56 and back again through transition region 58 to minimum in region 60, with a concurrent variation of extruded OD so that the OD is largest in the central region 56. This can be produced by varying the die gap B to open concurrently with narrowing of the tank gap, and to narrow the die gap again as the tank gap is widened. In this way the body diameter and/or wall thickness obtainable from the parison is increased relative to the waist diameter or wall thickness utilized.

Thus, while an increase in the hoop strength and modulus comes at the expense of thinner balloon walls, which can increase distention and decrease burst pressure, it is also possible to extrude tubes with lower elongation to break in the body section. This allows one to provide even stronger walls than were previously been obtained with a given polymer. Alternatively, the invention can allow one to thicken the balloon wall, while affecting the hoop strength and distension very little, thereby obtaining a balloon which is more suited to stent or other surgical device delivery operations.

In embodiments where the length of the transition from high to low orientation is desirably very short, as in the case of a balloon parison tube transitioning within a short region slated to form the balloon cone, moving a bath fast enough to change the orientation within such short region while running at suitable extrusion line speeds may become prohibitively difficult. However, the invention can be implemented using a modified cooling apparatus, such as is illustrated schematically in FIG. 4. Such an apparatus and the cooling method it implements represent still further aspects of the present invention.

Figure 4:
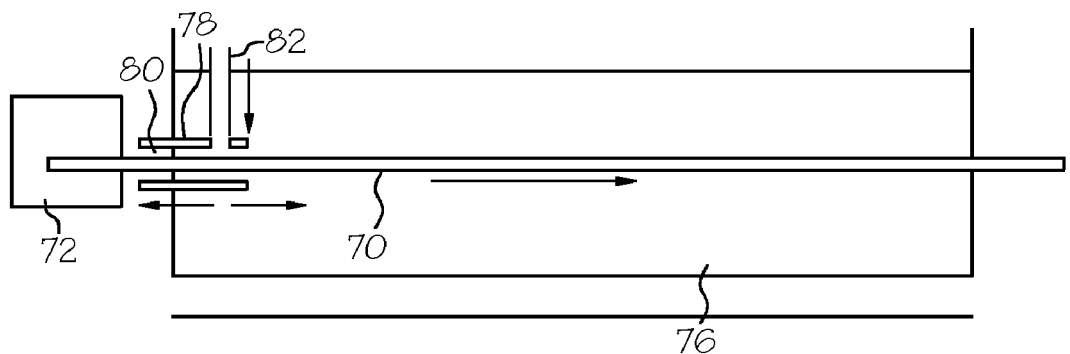
FIG. 4 is a schematic depiction of an extrusion system usable in the invention comprising a novel cooling apparatus which constitutes a further aspect of the invention.

In FIG. 4, a tube 70 of extruded thermoplastic material is shown emerging from an extruder head 72, passing through a standard cold water cooling bath 76. Prior to entering the water bath the extruded tube must first pass through a cooling pipe 78 made of a very high thermal conductivity material, for instance silver. A minimal annular coolant fluid gap 80 is provided between the extruded tube 70 and the inner wall of the cooling pipe 78. A coolant fluid is provided through a inlet 82 at a slow flow rate, and the cooling pipe is maintained at a uniform low temperature using, e.g. cooling fins, not shown, on the outside of the pipe or a flow of cooling liquid over the pipe, or and/or immersion of at a portion of the pipe length in the cooling bath 76.

The coolant fluid is fed into the cooling pipe via inlet 82 passes through the gap 80, conducting heat radially outward to the highly conductive walls of pipe 78. Water might be used as coolant fluid, but it might transition to steam, complicating its use. Suitably, the coolant fluid is a gas such as air, helium or hydrogen, or mixtures thereof.

There are several ways in which the orientation of the extruded tube 70 may be provided with varying orientation in short distances. Using air as conducting gas, the efficiency of the system goes down with a factor of 7 (−7) compared to using hydrogen. With helium versus air, the conductivity factor is −5 for air. When using water as a conductor instead of hydrogen or helium, a quicker cooling by a factor +2.8 can be established. Consequently, by rapidly switching cooling fluids, e.g. between air and hydrogen, one can rapidly achieve a change in the distance required to cool the extruded tube 70.

Also, the pipe 78 can be moved axially along the polymer tube very rapidly. The mass is low compared to moving the whole cooling bath. A motor, not shown, can be provided to change the gap distance between the extruder head 72 and the pipe 78.

In an alternative embodiment, instead of blowing air from within the cooling bath, one can also blow gas from the other side by closing at least a portion of the volume between the extruder head and the cooling bath and providing the coolant fluid feed through the closure.

The following is an example of how the invention can be implemented with a silver pipe cooling tube as described herein.

The extruder is run at a line-speed of a 0.2 [meter/second]. The tube being extruded is nylon with an OD of 1.5 mm and an ID of 1.0 mm.

Using the following parameters (all at 95° C.):
Nylon:
Specific heat 1700 [J/kg-C]
Heat conductivity 0.242 [W/m-C]
Density is 1100 [kg/m$^3$]
Water:
Specific heat 4204 [J/kg-C]
Heat conductivity 0.678 [W/m-C]
Density 963 [kg/m$^3$]
Silver:
Specific heat 230 [J/kg-C]

Heat conductivity 418 [W/m-C]
Density 10510 [kg/m$^3$]
Helium:
Specific heat 5200 [J/kg-C]
Heat conductivity 0.169 [W/m-C]
Density 0.13 [kg/m$^3$]

(The conductivity of air is 0.03365 [W/m-C]. So helium gas has a 5 times higher conductivity than air. Hydrogen is even better than helium, hydrogen having a conductivity of 0.228 [W/m-C] or 6.7 times higher than air.)

A silver pipe is provided enclosing the extruded tube with a small gap (0.3 mm) The silver pipe is immersed in the water bath with cooling fins on the outside to assure that the pipe is at a uniform temperature being equal to the water temperature. The water is at about 0 degrees Celsius. The extruded nylon tube exits the extruder at 180° C., directly entering the silver pipe, and one blows helium gas at low speed through the annular space in between the pipe and the tube. One can calculate the decrease in temperature of the tube quite easily taking a frame which moves at the same speed as the tube. In other words, one gets a static two dimensional heat problem of a number of a hot ring inside a cold environment with a spacing. Heat capacity, volumes, and other physical properties are given above. Now one can solve the system in polar coordinates. The flow in axial or tangential direction is zero, there is only flow in radial direction.

The net heat transfer is in the direction of the negative of the temperature gradient. Therefore:

$$Q/t = -k.L.2.Pi.Ln(r1/(r1-r_0)).(T(r1)-T(t0)), \text{ or}$$

$$Q = \text{Constant}. \Delta T. dt.$$

T(r1)=temperature at silver pipe surface=0 degrees.
Take a piece of the tube being 1 mm in height.
The volume of that piece is $3.12510^{-10}$ m$^3$, the weight is $3.438 \, 10^{-7}$ [kg]
The energy stored therefore is 0.1052 [Joule] (from 0 degrees=5.844E-4 [Joule/C])

Figure 5:
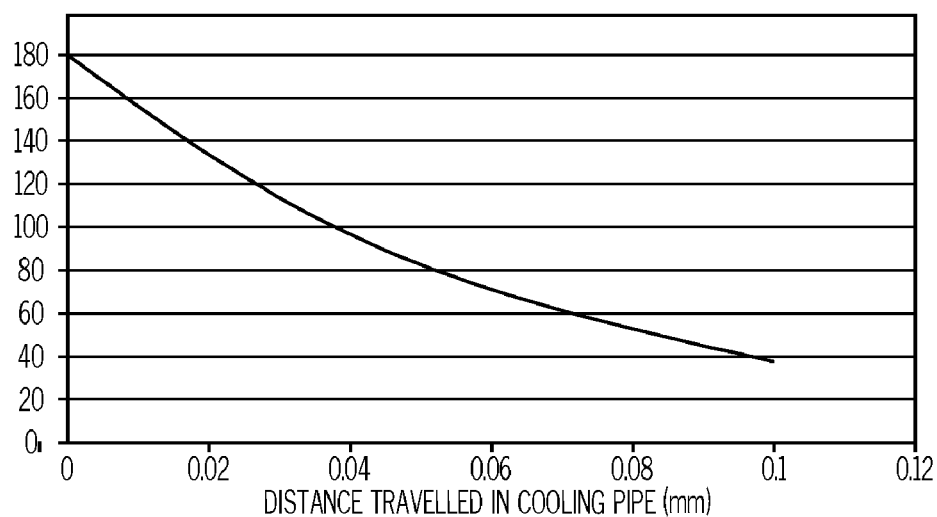
FIG. 5 is a graph of calculated cooling time versus axial distance traveled for a tubular extrusion drawn through a cooling apparatus as depicted in FIG. 4.

Taking a gap of 0.3 mm between the pipe and the tube, and using helium as the coolant fluid, one gets a decrease of the temperature in time as shown in FIG. 5. Similar calculations can be done using hydrogen as coolant fluid, using different gaps, or using air or water as the coolant fluid. The distances needed to effect cooling are short enough that their manipulation allows for the practical production of tubes having variation of orientation properties as described above.

The heat conductive pipe cooling system can also be implemented in more conventional extrusions which do not contemplate a variation of orientation properties along the extrusion length. The cooling capacity of existing cooling baths can be substantially increased so that the length of these baths can be significantly reduced. In some cases it may be possible to eliminate the use of water, and of blowers or other techniques currently employed to remove water from the extruded tubes.

The invention may be used with any known balloon materials. Examples include the polyesters PET, PEN, PPT, PBT and copolymers thereof, polyvinyl chloride, irradiated polyethylene, ultra-high molecular polyolefins, olefin ionomers (copolymers of olefin monomers and a metal salt of an olefinic acid, such as (meth)acrylic acid, maleic acid or fumaric acid) polyamides including aliphatic and aromatic nylons, polyurethane and various thermoplastic elastomers. High strength thermoplastic elastomers are preferred, especially polyamide/polyether block copolymers, including polyamide/polyether/polyesters such as sold under the PEBAX trademark, in particular PEBAX 7033 and PEBAX 7233; polyester/polyether block copolymers such as sold under the HYTREL and ARNITEL trademarks, in particular ARNITEL EM 740 and HYTREL 8238; and polyurethane block copolymers such as PELLETHANE 2363-75D. The parison may be extruded as a single layer or in multiple layers, for instance 3, 5, 7, or even more alternating layers of different polymers or polymer compositions. The layer or layers may be reinforced with liquid crystal polymer fibers or, Blends of two or more such polymers may also be used.

In one preferred embodiment of the invention, balloon formation is begun by extruding a tube from a melt of the polymer material in accordance with the present invention and cutting it to a segment having the orientation variations as described herein, thereby forming the balloon parison. The parison is then optionally conditioned at 20-30° C. at a controlled humidity for a period of at least 24 hours.

The parison may then be physically stretched longitudinally, optionally with heating and/or pressurization sufficient to prevent collapse of the ID of the tube, before blow forming the balloon. Alternatively, the parison may be stretched longitudinally concurrently with the blow forming step. In either case, the orientation difference between parison portions slated to form the body, cones and waists, respectively, will allow more material to be drawn longitudinally from the cone and waist slated regions of the parison than the body slated region(s).

The blow forming step is a conventional one or two step process involving pressurizing the parison with heating in known manner. Typically in a one step process the parison will be placed in a mold, the mold will be heated and the parison pressurized concurrently to expand the body slated portion of the parison to the mold diameter. In a typical two step process the parison is first free-blown to a diameter about 50-90% of the final diameter and then the partially blown balloon is placed in a mold heated to a higher temperature and pressurized to expand the balloon to the final diameter. A similar two-step blowing process is described in U.S. Pat. No. 4,963,313.

The total axial stretch ratio is suitably from about 2× to about 8× relative to original length of extruded tubing segment. The radial stretch ratio of the balloon is suitably from about 3× to about 15×.

In some cases a heat set, or heat shrink, step may also be utilized. In a heat set step the blown balloon, pressurized sufficiently to prevent shrinkage, is heated to a temperature above the blowing temperature. Under these conditions crystallization of the polymer material increases. In a heat shrink step the blown balloon under less pressure than utilized for blowing is heated, typically to a temperature above the glass transition of the material, but below the blowing temperature. Under these conditions the polymer material relaxes somewhat so that the initial diameter is reduced, although the balloon burst diameter and pressure will be largely unaffected.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A polymeric tubing segment, the tubing segment comprising first, second and third regions disposed sequentially along the length thereof,
   wherein the polymer disposed in said first region has a different longitudinal extruded orientation from the polymer disposed in said second region and
   said different longitudinal extruded orientations provide an elongation at yield of the polymeric material in at least one of said regions that is at least 20% less than the elongation at yield of another of said regions, and wherein
   the tubing segment is a parison for a catheter balloon,
   the polymer disposed in said second region has a higher or lower longitudinal extruded orientation relative to the polymer disposed in both of the first and third regions, and wherein
   the polymeric tubing is produced by extrusion wherein the extrusion is controlled to provide the difference in longitudinal extruded orientation of the polymer between the second region and the first and third regions.

2. An extruded polymeric tubing segment as in claim 1 wherein the tubing material is a single polymer.

3. An extruded polymeric tubing segment as in claim 1 wherein the tubing is a coextruded laminate of at least two different polymers.

4. An extruded polymeric tubing segment as in claim 1 wherein the tubing material comprises a polymer blend.

5. An extruded polymeric tubing segment as in claim 1 wherein said first and second regions have different wall thicknesses relative to each other.

\* \* \* \* \*